United States Patent
Faig et al.

(10) Patent No.: US 10,940,103 B2
(45) Date of Patent: Mar. 9, 2021

(54) ELASTIC COSMETIC MASKS AND METHODS FOR TREATING SKIN

(71) Applicant: L'OREAL, Paris (FR)

(72) Inventors: Jonathan Faig, Madison, NJ (US); David Chan, Edison, NJ (US)

(73) Assignee: L'OREAL, Paris (FR)

( * ) Notice: Subject to any disclaimer, the term of this patent is extended or adjusted under 35 U.S.C. 154(b) by 429 days.

(21) Appl. No.: 15/899,449

(22) Filed: Feb. 20, 2018

(65) Prior Publication Data

US 2018/0182451 A1    Jun. 28, 2018

(51) Int. Cl.

| | | |
|---|---|---|
| A61K 8/73 | (2006.01) | |
| A61K 8/02 | (2006.01) | |
| A61K 8/42 | (2006.01) | |
| A61Q 19/00 | (2006.01) | |
| A61K 8/34 | (2006.01) | |
| A61K 8/20 | (2006.01) | |
| A61Q 19/08 | (2006.01) | |
| A61K 8/25 | (2006.01) | |

(52) U.S. Cl.
CPC ............ *A61K 8/733* (2013.01); *A61K 8/0212* (2013.01); *A61K 8/20* (2013.01); *A61K 8/25* (2013.01); *A61K 8/345* (2013.01); *A61K 8/42* (2013.01); *A61Q 19/00* (2013.01); *A61Q 19/08* (2013.01)

(58) Field of Classification Search
CPC ........ A61K 8/0212; A61K 8/733; A61K 8/25; A61K 8/20; A61K 8/345; A61K 8/42; A61Q 19/00; A61Q 19/08
See application file for complete search history.

(56) References Cited

U.S. PATENT DOCUMENTS

| | | | | |
|---|---|---|---|---|
| 5,720,949 A | * | 2/1998 | Davis | A61K 8/0212 424/400 |
| 6,042,839 A | | 3/2000 | Lahanas et al. | |
| 6,623,751 B2 | | 9/2003 | Gueret | |
| 8,980,240 B2 | | 3/2015 | Jager Lezer et al. | |
| 2002/0025334 A1 | * | 2/2002 | Smith | A61K 9/7015 424/402 |
| 2003/0044366 A1 | | 3/2003 | Dole et al. | |
| 2006/0104931 A1 | | 5/2006 | Fukutome | |
| 2006/0147401 A1 | * | 7/2006 | Tanaka | A61Q 19/08 424/70.13 |
| 2006/0198805 A1 | | 9/2006 | Gupta | |
| 2007/0248633 A1 | | 10/2007 | Baldo | |
| 2010/0112058 A1 | | 5/2010 | Lim et al. | |
| 2010/0316577 A1 | | 12/2010 | Raineau | |
| 2011/0081307 A1 | | 4/2011 | Raineau | |
| 2013/0156831 A1 | * | 6/2013 | Matsuo | A61K 8/733 424/401 |
| 2014/0356402 A1 | | 12/2014 | Lemoine et al. | |
| 2015/0056296 A1 | * | 2/2015 | Hiki | A61K 8/19 424/613 |
| 2016/0158123 A1 | | 6/2016 | Agarwal et al. | |

FOREIGN PATENT DOCUMENTS

| | | |
|---|---|---|
| CN | 102911381 A | 2/2013 |
| FR | 2782923 A1 | 3/2000 |
| WO | WO-2019/045935 A1 | 3/2019 |

OTHER PUBLICATIONS

"Laponite," PubChem at https://pubchem.ncbi.nlm.nih.gov/compound/ Lithium-magnesium-sodium-silicate, printed May 31, 2020.*
"Hectorite," PubChem at https://pubchem.ncbi.nlm.nih.gov/compound/ 72941499, printed May 31, 2020.*
"Hydrating Modeling Mask", Dr. Dennis Gross;—http://www.gnpd.com.
International Search Report and Written Opinion dated May 27, 2019 for corresponding PCT Application No. PCT/US2019/018459.

* cited by examiner

*Primary Examiner* — Susan S Su
(74) *Attorney, Agent, or Firm* — Polsinelli PC

(57) ABSTRACT

The instant disclosure relates to masks, methods for making masks, methods for improving film elasticity of masks, and to methods of treating skin with masks. The masks are formed by applying a mask base composition onto a surface, the mask base composition comprising: (i) alginic acid and/or a salt thereof; (ii) hectorite (lithium magnesium sodium silicate); (iii) one or more water-soluble solvents; and (iv) water; and exposing the mask base composition to a crosslinking composition for a time sufficient to crosslink the alginic acid and/or a salt thereof and form a final mask, the crosslinking composition being an aqueous liquid comprising (i) one or more polyvalent cations of one or more metals; and (ii) water. The instant disclosure further relates to masks formed by the disclosed methods and to kits comprising the compositions for making and/or using the masks.

19 Claims, No Drawings

ELASTIC COSMETIC MASKS AND METHODS FOR TREATING SKIN

FIELD OF THE DISCLOSURE

The instant disclosure relates to masks, to methods for making the masks, to methods for improving the elasticity of the masks, and to cosmetic methods for treating skin with the masks.

BACKGROUND

Skin acts as a natural barrier between the internal and the external environment and therefore plays an important role in vital biological functions such as protection against mechanical and chemical injury, micro-organisms, and ultraviolet damage. Skin, however, is delicate, is easily damaged, and tends to lose its youthful appearance with age. Consumers are interested in finding ways to minimize damage and the aging process of skin. To achieve the appearance of healthy and youthful looking skin, consumers utilize a variety of skin care products, diet supplements, and beautification methods.

In addition to the natural aging process, UV light contributes to the aging of skin by causing free radicals to form. Free radicals include, for example, singlet oxygen, hydroxyl radical, the superoxide anion, nitric oxide and hydrogen radicals. Free radicals attack DNA, membrane lipids and proteins, generating carbon radicals. These in turn react with oxygen to produce a peroxyl radical that can attack adjacent fatty acids to generate new carbon radicals. This cascade leads to a chain reaction producing lipid peroxidation products. Damage to cell membranes results in loss of cell permeability, increased intercellular ionic concentration, and decreased ability to excrete or detoxify waste products. The end result is a loss of skin elasticity and the appearance of wrinkles. This process is commonly referred to as photoaging.

One method that has been used to improve the appearance of skin, especially the skin of the face and neck, is the use of facial masks. Facial masks are used for a variety of reasons, including: deep-cleansing, by penetrating the pores; healing acne scars or hyper-pigmentation; and brightening, for a gradual illumination of the skin tone.

There are a few different types of masks. Some masks are designed to dry or solidify on the face, while others remain wet. Clay masks can help draw oil and dirt to the surface of the skin. As the name indicates, clay masks include clay(s), which help provide tightening and sebum-absorbing effects. Cream masks or gel masks are often formulated to hydrate and nourish the skin. Setting masks harden into a rubbery state, and therefore setting masks can be peeled away from the face after use by the user or an aesthetician.

Duration for wearing a mask varies with the type of mask and the manufacturer's usage instructions, and may range from a few minutes to overnight. After use, a mask is typically removed by rinsing with water, wiping off with a damp cloth, or by peeling the mask away from the skin. While it may be desirable to simply peel a mask away from the skin, this has been difficult with known mask compositions, which tend to break into pieces while leaving residue behind.

SUMMARY OF THE DISCLOSURE

The instant disclosure relates to masks and in particular to cosmetic masks for treating skin such as the skin of the face and neck. The inventors discovered that lithium magnesium sodium silicate, unlike other clays, provides unexpected elasticity to alginate-based masks. The improved elasticity contributes to better aesthetics, reduced brittleness, and easier removal of the mask from skin. Another unique feature of the masks is that they can be formed in situ, e.g., the masks can be formed on the face of an individual. A mask base composition is initially spread onto an area to be treated (e.g., the face of an individual). An aqueous crosslinking solution is then applied to the mask base composition (the mask base composition that is already on an area to be treated) to crosslink alignate in the mask base composition. The resulting mask therefore perfectly matches the shape and contour of the face. Additionally, the elastic nature of the mask is comfortable and allows for movement of the face while wearing the mask without cracking or breaking the mask.

The masks are formed by applying a mask base composition onto a surface, the mask base composition comprising:
  (i) alginic acid and/or a salt thereof;
  (ii) lithium magnesium sodium silicate;
  (iii) one or more water-soluble solvents; and
  (iv) water;
and exposing the mask base composition to a crosslinking composition for a time sufficient to crosslink the alginic acid and/or a salt thereof and form a final mask, the crosslinking composition being an aqueous liquid comprising:
  (i) one or more polyvalent cations of one or more metals; and
  (ii) water.

The final masks exhibit improved elasticity in comparison to analogous masks that do not include lithium magnesium sodium silicate, and in comparison to analogous masks having the lithium magnesium sodium silicate replaced with other clays.

The mask base composition is typically in a form that is easily spread or applied to skin (e.g., a cream, paste, gel, etc.). This allows for the mask base composition to be conventinely applied and spread onto skin using the fingers or hands if desired. Nonetheless, other methods of applying the mask base composition may certainly be employed.

The crosslinking composition is an aqueous liquid that is typically less viscous than the mask base composition. The aqueous liquid usually has a fluidity allowing it to be sprayable. Therefore, the crosslinking composition can be conveniently applied to the mask base composition by spraying. The time sufficient for the crosslinking composition to crosslink alginic acid and/or a salt thereof in the mask base composition is typically very quick, less than five minutes, but in many instances much faster, for example, one minute or less. Upon crosslinking, the final mask is formed. The final mask is usually more solid or rigid than the mask base composition due to the crosslinking reaction. Thus, the final mask may be a solid composite having an elastic texture or may be a thickened cream, paste, gel, or semi-solid material.

The instant disclosure also relates to masks formed by the methods described herein and to kits comprising the various components and/or compositions for use in the methods disclosed herein. For example, a kit may include:
  (a) a mask base composition comprising:
    (i) alginic acid and/or a salt thereof;
    (ii) lithium magnesium sodium silicate;
    (iii) one or more water-soluble solvents; and
    (iv) water; and (b) a crosslinking composition comprising:
   (i) one or more polyvalent cations of one or more metals; and
   (ii) optionally, water;
wherein the mask base composition and the crosslinking composition are separately contained. In some cases, however, the lithium magnesium sodium silicate may be separate from the mask base composition in the kit, resulting in a kit that includes:
   (a) a mask base composition comprising:
      (i) alginic acid and/or a salt thereof;
      (ii) one or more water-soluble solvents; and
      (iii) water;
   (b) a composition comprising lithium magnesium sodium silicate; and
   (c) a crosslinking composition comprising:
      (i) one or more polyvalent cations of one or more metals; and
      (ii) optionally, water;
wherein the mask base composition, the composition comprising lithium magnesium sodium silicate, and the crosslinking composition are separately contained.

The masks of the instant disclosure are particularly effective for treating skin, especially the skin of the face and neck. Thus, the instant disclosure relates to methods for treating skin including the skin of the face and neck. For example, the instant disclosure includes methods for: (1) reducing the appearance of fine lines in skin; (2) reducing the appearance of wrinkles in skin; (3) improving the appearance of skin tone and/or skin tone evenness; (4) imparting softness to skin; (5) improving the radiance, luminosity, and/or glow of skin; (6) hydrating the skin; and/or (7) deliver one or more skin active ingredients to the skin. The methods include forming a mask on the skin (as described above), allowing the mask to remain on the skin for a period of time, and removing the mask from the skin.

DETAILED DESCRIPTION OF THE DISCLOSURE

The instant disclosure relates to masks, methods for making the masks, methods for improving the elasticity of the masks, and to cosmetic methods for treating skin with the masks. The methods typically include
   (a) applying a mask base composition onto a surface, the mask base composition comprising:
      (i) alginic acid and/or a salt thereof;
      (ii) lithium magnesium sodium silicate;
      (iii) one or more water-soluble solvents; and
      (iv) water; and
   (b) exposing the mask base composition to a crosslinking composition for a time sufficient to crosslink the alginic acid and/or a salt thereof and form a final mask, the crosslinking composition being an aqueous liquid comprising:
      (i) one or more polyvalent cations of one or more metals; and
      (ii) water.

The mask base composition is applied to a surface such as skin (and in particular the skin of the face and neck). The mask base composition may be applied to provide a substantially uniform thickness of about 1 to about 25 mm. The thickness may also be about 1 to about 20 mm, about 1 to about 15 mm, about 1 to about 10 mm, about 1 to about 5 mm, about 2 to about 25 mm, about 2 to about 20 mm, about 2 to about 15 mm, about 2 to about 10 mm, about 2 to about 8 mm, about 2 to 5 mm, or about 3 mm. The amount of mask base composition applied to the surface largely determines the thickness of the final mask because the crosslinking composition adds little, if any, appreciate thickness to the final mass. Accordingly, the thickness of the final mask may vary but is typically about 1 to about 25 mm. The thickness of the final mask may be about 1 to about 20 mm, about 1 to about 15 mm, about 1 to about 10 mm, about 1 to about 5 mm, about 2 to about 25 mm, about 2 to about 20 mm, about 2 to about 15 mm, about 2 to about 10 mm, about 2 to about 8 mm, about 2 to 5 mm, or about 3 mm.

The final masks exhibit improved elasticity in comparison to analogous final masks that do not include lithium magnesium sodium silicate. For example, the final masks typically have an elongation to break at 25° C. that is at least 10%, 25%, 50%, 75%, 100%, or 150 (up to about 200% or 300%) higher than that of an analogous final mask not containing lithium magnesium sodium silicate. Similarly, the final masks may have an elongation to break at 25° C. that is at least 10%, 25%, 50%, 75%, 100%, or 150 (up to about 200% or 300%) higher than that of an analogues final mask having the lithium magnesium sodium silicate substituted with the same amount of another clay such as another smectite clay (e.g., kaolin or montmorillonite) or mica.

The time sufficient to crosslink alginic acid and/or a salt thereof and form a final mask may vary and can depend on the concentration and type of polyvalent cations of the one or more metals in the crosslinking composition; and can also vary depending on the amount of crosslinking composition applied to the mask base composition. Nonetheless, the time sufficient to crosslink alginic acid and/or a salt thereof and form a final mask is usually less than 5 minutes. In particular, the time sufficient to crosslink alginic acid and/or a salt thereof and form a final mask may be 4 minutes or less, 3 minutes or less, 2 minutes or less, or 1 minute or less. Typically the crosslinking reaction occurs nearly instantaneously upon exposure of the mask base composition to the crosslinking composition. Therefore, crosslinking begins within a few seconds of applying the crosslinking composition to the mask base composition.

The mask base composition is typically in a form that can easily be spread or applied to skin (e.g., a cream, paste, gel, etc.). This allows for the mask base composition to be applied and spread onto skin using the fingers or hands if desired. The crosslinking composition, however, is an aqueous liquid that is typically less viscous than the mask base composition. The aqueous liquid usually has a fluidity allowing it to be sprayable. Therefore, the crosslinking composition may conveniently be applied onto the mask base composition by spraying. Upon crosslinking, a final mask is formed. The final mask is usually more solid or rigid than the mask base composition due to the crosslinking reaction. For example, the final mask may be a solid composite having an elastic texture or may be a thickened (or rigid) cream, paste, gel, or semi-solid material.

As touched on above, the crosslinking composition is an aqueous liquid that typically has a fluidity allowing it to be sprayable. Thus, in some instances, the crosslinking composition may be applied to the mask base composition by spraying, for example with a pump sprayer or as an aerosol. An amount of crosslinking composition sufficient to crosslink alginic acid and/or a salt thereof is applied to the mask base composition. A sufficient amount is typically an amount that uniformly covers the surface of the mask base composition. The crosslinking composition may be applied to the mask base composition in an amount of about 1 to 10 grams of crosslinking composition per 100 $cm^2$ of mask base composition. In some cases, the crosslinking composition may be applied to the mask base composition in an amount of about 1 to 8 grams, about 1 to 6 grams, about 2 to 6 grams, or about 3 to 5 grams of crosslinking composition per 100 cm² of mask base composition.

Mask Base Composition

The mask base composition includes alginic acid and/or a salt thereof, lithium magnesium sodium silicate, one or more water-soluble solvents, and water. The mask base composition typically includes very little or no polyvalent metal cations so that premature crosslinking of the alginic acid and/or a salt thereof in the mask base composition is avoided. For example, the maximum content of polyvalent metal cations in the mask base composition may be 5%, 4%, 3%, 2%, 1%, 0.5%, 0.2%, 0.1%, 0.05%, 0.02%, 0.01% or less on a weight basis, relative to the total amount of alginic acid and/or a salt thereof in the mask base composition. Accordingly, the mask base composition is typically free or essentially free of added polyvalent metal cations (e.g., calcium ions), which means that the mask base composition does not include polyvalent metal cations (e.g., calcium ions) other than those that may be naturally present in the alginate or other raw materials of the mask base composition.

(i) Alginic Acid and Salts

Alginic acid (sometimes referred to in the literature as "alginate" or "algin") is an anionic polysaccharide distributed widely in the cell walls of algae. Alginic acid is a linear copolymer with homopolymeric blocks of (1-4)-linked β-D-mannuronate (M) and its C-5 epimer α-L-guluronate (G) residues, respectively, covalently linked together in different sequences or blocks. The monomers can appear in homopolymeric blocks of consecutive G-residues (G-blocks), consecutive M-residues (M-blocks) or alternating M and G-residues (MG-blocks).

Non-limiting examples of salts of alginic acid (alginates) include sodium alginate, potassium alginate, magnesium alginate, calcium alginate, propylene glycol alginate, ammonium alginate, triethanolamine alginate, or any combinations thereof. In some instances, the mask base compositions preferably include alginic acid, sodium alginate, potassium alginate, or a mixture thereof, because they are particularly water-soluble.

The total amount of alginic acid and/or salts thereof in the mask base composition may vary but is typically about 0.1 to about 20 wt. %, based on the total weight of the mask base composition. The total amount of alginic acid and/or salts thereof in the mask base composition may be about 0.1 to about 15 wt. %, about 0.1 to about 10 wt. %, about 0.1 to about 5 wt. %, about 0.5 to about 20 wt. %, about 0.5 to about 15 wt. %, about 0.5 to about 10 wt. %, about 0.5 to about 5 wt. %, about 1 to about 20 wt %, about 1 to about 15 wt. %, about 1 to about 10 wt. %, or about 1 to about 5 wt. %, based on the total weight of the mask base composition.

(ii) Lithium Magnesium Sodium Silicate

The lithium magnesium sodium silicate can be hectorite and/or laponite. Hectorite is naturally occurring clay and laponite is a synthetic silicate clay consisting mainly of lithium, magnesium and sodium silicates. The total amount of lithium magnesium sodium silicate in the mask base composition may vary but is typically about 0.1 to about 20 wt. %, based on the total weight of the mask base composition. The total amount of lithium magnesium sodium silicate in the mask base composition may be about 0.1 to about 15 wt. %, about 0.1 to about 10 wt. %, about 0.1 to about 5 wt. %, about 0.5 to about 20 wt. %, about 0.5 to about 15 wt. %, about 0.5 to about 10 wt. %, about 0.5 to about 5 wt. %, about 1 to about 20 wt. %, about 1 to about 15 wt. %, about 1 to about 10 wt. %, or about 1 to about 5 wt. %, based on the total weight of the mask base composition.

The ratio of the total amount of the alginic acid and salts thereof to the total amount of lithium magnesium sodium silicate in the mask base composition may vary but is typically about 1:10 to about 10:1. The ratio of the total amount of the alginic acid and salts thereof to the total amount of lithium magnesium sodium silicate in the mask base composition may be about 1:8 to about 8:1, about 1:5 to about 5:1, about 1:3 to about 3:1, or about 1:2 to about 2:1.

In some instances it may be useful to include a greater total amount of lithium magnesium sodium silicate than the total amount of alginic acids and salts thereof. For example, the ratio of the total amount of the alginic acid and salts thereof to the total amount of lithium magnesium sodium silicate in the mask base composition may be 1:(greater than 1) to about 1:10, 1:(greater than 1) to about 1:8, 1:(greater than 1) to about 1:5, 1:(greater than 1) to about 1:3, 1:1.2 to about 1:10, 1:1.2 to about 1:8, 1:1.2 to about 1:5, or about 1:1.2 to about 1:3.

(iii) Water-Soluble Solvent

The mask base composition typically includes at least one water-soluble solvent. The term "water-soluble solvent" is interchangeable with the term "water-miscible solvent" and means a compound that at 25° C. and at atmospheric pressure (760 mmHg) has a solubility of at least 50% in water. In some cases, the water-soluble solvent has a solubility of at least 60%, 70%, 80%, or 90% in water at 25° C. and at atmospheric pressure (760 mmHg). Non-limiting examples of water-soluble solvents include, for example, glycerin, alcohols (for example, $C_{1-8}$ or $C_{1-4}$ alcohols), organic solvents, polyols, glycols, and a mixture thereof.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents include alkanols (polyhydric alcohols such as glycols and polyols) such as glycerin, 1,2,6-hexanetriol, trimethylolpropane, ethylene glycol, propylene glycol, diethylene glycol, butylne glycol, hexylene glycol, triethylene glycol, tetraethylene glycol, pentaethylene glycol, dipropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

In some cases, the water-soluble solvent may be selected from the group consisting of one or more glycols, $C_{1-4}$ alcohols, glycerin, and a mixture thereof.

The total amount of the one or more water-soluble solvents may vary but is typically about 0.1 to about 50 wt. %, based on the total weight of the mask base composition. The total amount of the one or more water-soluble solvents may be about 0.1 to about 40 wt. %, about 0.1 to about 30 wt. %, about 0.1 to about 20 wt. %, about 1 to about 50 wt. %, about 1 to about 40 wt. %, about 1 to about 30 wt. %, about 1 to about 20 wt. %, about 5 to about 50 wt. %, about 5 to about 40 wt. %, about 5 to about 30 wt. %, or about 5 to about 20 wt. %, based on the total weight of the mask base composition.

(iv) Water

The total amount of water in the mask base composition may vary but is typically in an amount of about 40 to about 95 wt. %, based on the total weight of the mask base composition. In some instances, the total amount of water in the mask base composition is about 50 to about 95 wt. %, about 60 to about 95 wt. %, about 70 to about 95 wt. %, about 40 to about 90 wt. %, about 40 to about 50 to about 90 wt. %, about 60 to about 90 wt. %, or about 70 to about 90 wt. %, based on the total weight of the mask base composition.

Crosslinking Composition

The crosslinking composition is an aqueous liquid containing one or more polyvalent cations of one or more metals, for example, trivalent or divalent metal cations, which act as crosslinking agents.

(i) Polyvalent Cations of Metals

Non-limiting examples of trivalent or divalent metal cations include Ca, Cu, Zn, Al, and Fe (ferrous or ferric) cations, as well as Zr-containing cations. For example, any of these may be present as a salt. The salt may be one with an inorganic counterion, for example, nitrate, chloride, sulfate, or phosphate. Alternatively, the counterion may be an organic counterion, for example acetate, ascorbate, citrate, or pidolate. In some cases, an aqueous solution of calcium chloride is a particularly useful crosslinking composition.

The total amount of salts in the crosslinking composition that provide the one or more polyvalent cations of one or more metals may vary but is typically about 0.1 to about 35 wt. %, based on the total weight of the crosslinking composition. The total amount of salts in the crosslinking composition that provide the one or more polyvalent cations of one or more metals may be about 0.1 to about 30 wt. %, about 0.1 to about 25 wt. %, about 0.1 to about 20 wt. %, about 0.1 to about 15 wt. %, about 0.1 to about 10 wt. %, about 0.1 to about 5 wt. %, about 0.5 to about 30 wt. %, about 0.5 to about 25 wt. %, about 0.5 to about 20 wt. %, about 0.5 to about 15 wt. %, about 0.5 to about 10 wt. %, about 0.5 to about 5 wt. %, about 1 to about 30 wt. %, about 1 to about 20 wt. %, about 1 to about 15 wt. %, about 1 to about 10 wt. %, or about to about 5 wt. %, based on the total weight of the crosslinking composition.

(ii) Water

The total amount of water in the crosslinking composition may vary but is typically about 50 to about 99 wt. %, based on the total weight of the crosslinking composition. The total amount of water in the crosslinking composition may be about 60 to about 99 wt. %, about 70 to about 99 wt. %, about 80 to about 99 wt. %, about 85 to about 99 wt. %, about 50 to about 95 wt. %, about 60 to about 95 wt. %, about 70 to about 95 wt. %, about 80 to about 95 wt. %, or about 85 to about 95 wt. %, based on the total weight of the crosslinking composition.

The methods for making a mask, methods for improving the elasticity of a mask, and to method for treating skin, according to the instant disclosure, include:

(a) applying a mask base composition onto a surface (such as skin, in particular, the skin of the face and neck), the mask base composition comprising:
  (i) about 0.1 to about 15 wt. %, about 0.5 to about 10 wt. %, or about 1 to about 5 wt. %, based on the total weight of the mask base composition, of alginic acid and/or a salt thereof;
  (ii) about 0.1 to about 20 wt. %, about 0.5 to about 15 wt. %, or about 1 to about 10 wt. %, based on the total weight of the mask base composition, of lithium magnesium sodium silicate;
  (iii) about 0.1 to about 50 wt. %, about 1 to about 40 wt. %, or about 5 to about 20 wt. %, based on the total weight of the mask base composition, of one or more water-soluble solvents, for example, one or more water-soluble solvents selected from the group consisting of glycerin, alcohols (e.g., $C_{1-8}$ alcohols), organic solvents, polyols, glycols, and a mixture thereof; and
  (iv) about 40 to about 95 wt. %, about 50 to about 95 wt. %, or about 60 to about 95 wt. %, based on the total weight of the mask base composition, of water; and (b) exposing the mask base composition to a crosslinking composition for a time sufficient to crosslink the alginate and form a final mask, for example a time of about 5 minutes or less, the crosslinking composition being an aqueous liquid comprising:
  (i) about 0.1 to about 35 wt. %, about 0.5 to about 30 wt. %, or about 1 to about 20 wt. %, based on the total weight of the crosslinking composition, of salt(s) that provide one or more polyvalent cations of one or more metals; and
  (ii) about 50 to about 99 wt. %, about 60 to about 99 wt. %, or about 70 to about 95 wt. %, based on the total weight of the crosslinking composition, of water.

The mask base composition is preferably exposed to the crosslinking composition by spraying. In other words, the crosslinking composition is preferably applied to the mask base composition as a spray.

Methods for treating skin may further include allowing the final mask to remain on the skin for a period of time. The period of time may vary depending on the treatment and ultimate objective for using the mask. For example, the mask may be allowed to remain on the skin overnight or for a period of up to 10 hours, up to 8 hours, up to 6 hours, up to 4 hours, up to 2 hours, or up to 1 hour. Shorter periods of time are also useful. For example, the mask may be allowed to remain on the skin for about 1 minute to about 30 minutes, about 1 minute to about 20 minutes, about 1 minute to about 15 minutes, about 1 minute to about 10 minutes, about 5 minute to about 30 minutes about 5 minutes to about 20 minutes about 5 minutes to about 15 minutes, or about 5 minutes to about 10 minutes. After allowing the final mask to remain the skin for a period of time, the final mask is removed from the skin. The final mask may be removed by sampling peeling the final mask away from the skin and optionally rinsing the face with water (or cleansing the face with a cleanser and water). At the end of the desired time, the mask may be easily removed by peeling, leaving very little residue on the skin. Typically, the mask can be peeled from a user's skin in at most three pieces, or at most two pieces. I particular, the mask can be peeled in a single piece.

In addition to the various components specifically set forth above for the mask base composition and the crosslinking composition, many additional components may optionally be included in these compositions (or optionally excluded). For example, the mask base compositions and/or the crosslinking compositions of the instant disclosure may include (or exclude), clays in addition to the lithium magnesium sodium silicate, for example mica, film forming polymers, surfactants, emulsifiers, thickening agents, silicones, fatty acids, fatty alcohols, colorants, perfumes/fragrances, preservatives, skin active ingredients, emollients, oils, etc.

One or more water-soluble solvents have been described above for inclusion in the mask base compositions. In some instances, the crosslinking composition may also include one or more water-soluble solvents, such as those described for the mask base composition. One or more water-soluble solvents (such as those outlined above for the mask base composition) may be included in the crosslinking composition in an amount of about 0.1 to about 50 wt. %, based on the total weight of the crosslinking composition. The total amount of the one or more water-soluble solvents may be about 0.1 to about 40 wt. %, about 0.1 to about 30 wt. %, about 0.1 to about 20 wt. %, about 1 to about 50 wt. %, about 1 to about 40 wt. %, about 1 to about 30 wt. %, about 1 to about 20 wt. %, about 5 to about 50 wt. %, about 5 to about 40 wt. %, about 5 to about 30 wt. %, or about 5 to about 20 wt. %, based on the total weight of the crosslinking composition.

In some instances, the mask base composition and/or the crosslinking composition of the instant disclosure may include one or more thickening agents. Many thickening agents are water-soluble, and increase the viscosity of water or form an aqueous gel when the dispersed/dissolved in water. The aqueous solution may be heated and cooled, or neutralized, for forming the gel, if necessary. The thickening agent may also or alternatively be dispersed/dissolved in water-soluble solvent. Non-limiting examples of thickening agents include polysaccharides (e.g., cellulose, xanthan gum, diutan gum, carrageenan, gellan gum, welan gum, pectin, sclerotium gum, starch, galactoarabinan, and modified-forms thereof); homopolymers of acrylic acid; acrylic acid cross-linked with a polyfunctional compound (e.g. carbomer and acrylate crosspolymer; copolymers of acrylic acid, acrylate esters, maleic acid and the like, generally known as the alkali swellable emulsions (ASE) group); hydrophobically-modified copolymers of acrylic acid, acrylate esters, maleic acid and the like, generally known as the hydrophobically-modified alkali swellable emulsions (HASE) group; polyethylene glycol units of varying length connected by urethane linkages and terminated with hydrophobic end groups, generally known as the hydrophobically-modified ethoxylated urethane resins (HEUR) group; organoclays; silicas; fatty acids; and combinations thereof. In some instances, the mask base composition preferably includes one or more polysaccharide thickening agents, for example, one or more selected from the group consisting of cellulose, xanthan gum, diutan gum, carrageenan, gellan gum, welan gum, pectin, sclerotium gum, starch, galactoarabinan, and modified-forms thereof.) A more exhaustive but non-limiting list of thickening agents that may be included (or excluded) is provided later, under the heading "Skin-Active Agents."

The total amount of the thickening agents when present in the mask base composition and/or the crosslinking composition may vary but is typically about 0.01 to about 10 wt. %, based on the total weight of the mask base composition or the crosslinking composition. The total amount of the thickening agents in the mask base composition may be about 0.01 to about 8 wt. %, about 0.01 to about 5 wt. %, about 0.01 to about 4 wt. %, about 0.01 to about 2 wt. %, about 0.05 to about 10 wt. %, about 0.05 to about 8 wt. %, about 0.05 to about 5 wt. %, about 0.05 to about 4 wt. %, about 0.05 to about 2 wt. %, based on the total weight of the mask base composition or the crosslinking composition.

In some instances, the mask base composition and/or the crosslinking composition may include one or more skin active agents. Non-limiting examples of skin active agents include adenosine, 2-[4-(2-hydroxyethyl)piperazin-1-yl]ethanesulfonic acid (HEPES), hyaluronic acid, lanolin, citric acid, malic acid, lactic acid, tartaric acid, salicylic acid, vitamin C, a vitamin, a retinoid, retinal, retinoic acid, a carotenoid, an amino acid, a protein, an enzyme, a coenzyme, and a mixture thereof. A more exhaustive but non-limiting list of skin-active agents that may be included (or excluded) is provided later, under the heading "Skin-Active Agents."

The total amount of the skin active agents in the mask base composition or the crosslinking composition may vary but is typically in an amount of about 10 ppm to 10 wt. % (100,000 ppm), 10 ppm to 5 wt. % (50,000 ppm), 10 ppm to 2.5 wt. % (25,000 ppm), 10 ppm to 1 wt. % (10,000 ppm), 10 ppm to 0.5 wt. % (5,000 ppm), 10 ppm to 0.1 wt. % (1,000 ppm), or 10 ppm to 500 ppm of one or more active ingredients. In some cases, the one or more active ingredients is present in an amount from 10, 20, 30, 40, 50, 60, 70, 80, 90, 100, 150, or 200 ppm to 500, 600, 700, 800, 900, 0.1 wt. % (1000 ppm), 0.5 wt. % (5,000 ppm), 1 wt. % (10,000 ppm)), 5 wt. % (50,000 ppm), or 10 wt. % (100,000 ppm).

When a component is excluded from the mask base composition and/or the crosslinking composition, the mask base composition and/or the crosslinking composition may be "free" or "essentially free" of the component. For instance, in some instances, the mask base composition and/or the crosslinking composition may be free or essentially free of one or more of: mica; polymeric film forming polymers (other than the alginic acid and/or salt thereof and the lithium magnesium sodium silicate); surfactants and/or emulsifiers (for example, non-ionic, anionic, cationic, and/or amphoteric (zwitterionic) surfactants and/or emulsifiers); oils; silicones; and/or synthetic ingredients.

In one embodiment, the mask base composition may include:
(i) about 0.1 to about 15 wt. %, about 0.5 to about 10 wt. %, or about 1 to about 5 wt. %, based on the total weight of the mask base composition, of alginic acid and/or a salt thereof, preferably sodium and/or potassium alginate;

(ii) about 0.1 to about 20 wt. %, about 0.5 to about 15 wt. %, or about 1 to about 10 wt. %, baed on the total weight of the mask base composition, of lithium magnesium sodium silicate;

(iii) about 0.1 to about 50 wt. %, about 1 to about 40 wt. %, or about 5 to about 20 wt. %, based on the total weight of the mask base composition, of one or more water-soluble solvents, for example, one or more water-soluble solvents selected from the group consisting of lycerin, alcohols (e.g., $C_{1-8}$ alcohols), organic solvents, polyols, glycols, and a mixture thereof;

(iv) about 40 to about 95 wt. %, about 50 to about 95 wt. %, or about 60 to about 95 wt. %, based on the total weight of the mask base composition, of water;

(v) optionally, one or more thickening agents, for example, about 0.01 to about 10 wt. %, about 0.01 to about 8 wt. %, or about 0.05 to about 6 wt. %, based on the total weight of the mask base composition, of one or more thickening agents, in particular, one or more polysaccharide thickening agents; and (vi) optionally, one or more skin-active agents, for example, about 10 ppm to about 10 wt. % (100,000 ppm), about 10 ppm to about 5 wt. % (50,000 ppm), about 10 ppm to about 2.5 wt. % (25,000 ppm), based on the total weight of the mask base composition, of one or more skin-active agents selected from the group consisting of adenosine, 2-[4-(2-hydroxyethyl)piperazin-1-yl]ethanesulfonic acid (HEPES), hyaluronic acid, lanolin, citric acid, malic acid, lactic acid, tartaric acid, salicylic acid, vitamin C, a vitamin, a retinoid, retinal, retinoic acid, a carotenoid, an amino acid, a protein, an enzyme, a coenzyme, and a mixture thereof.

In one embodiment, the crosslinking composition may include:

(i) about 0.1 to about 35 wt. %, about 0.5 to about 30 wt. %, or about 1 to about 20 wt. %, based on the total weight of the crosslinking composition, of salt(s) that provide one or more polyvalent cations of one or more metals;

(ii) about 50 to about 99 wt. %, about 60 to about 99 wt. %, or about 70 to about 95 wt. %, based on the total weight of the crosslinking composition, of water;

(iii) optionally, about 0.1 to about 50 wt. %, about 1 to about 40 wt. %, or about 5 to about 20 wt. %, based on the total weight of the crosslinking composition, of one or more water-soluble solvents, for example, one or more water-soluble solvents selected from the group consisting of lycerin, alcohols (e.g., $C_{1-8}$ alcohols), organic solvents, polyols, glycols, and a mixture thereof; and (v) optionally, one or more thickening agents, for example, about 0.01 to about 10 wt. %, about 0.01 to about 8 wt. %, or about 0.05 to about 6 wt. %, based on the total weight of the mask base composition, of one or more thickening agents, in particular, one or more polysaccharide thickening agents.

The instant disclosure also relates to kits comprising the various components and/or compositions for use in the methods for making and using the masks of the instant disclosure. For example, a kit may include:

(a) a mask base composition comprising:
(i) alginic acid and/or a salt thereof;
(ii) lithium magnesium sodium silicate;
(iii) one or more water-soluble solvents; and
(iv) water; and (b) a crosslinking composition comprising:
(i) one or more polyvalent cations of one or more metals; and
(ii) optionally, water;

wherein the mask base composition and the crosslinking composition are separately contained. The mask base composition and the crosslinking composition of the kit are generally outlined above but can be modified as described throughout this disclosure. In other words, all embodiments of the disclosure relating to mask base compositions and crosslinking compositions apply to kits comprising such compositions.

In some cases, kits according to the disclosure, may contain the lithium magnesium sodium silicate of the mask base composition as a separate components of the kit. Thus, a kit according to the disclosure may include:

(a) a mask base composition comprising:
(i) alginic acid and/or a salt thereof;
(ii) one or more water-soluble solvents; and
(iii) water;

(b) a composition comprising lithium magnesium sodium silicate; and (c) a crosslinking composition comprising:
(i) one or more polyvalent cations of one or more metals; and
(ii) optionally, water;

wherein the mask base composition, the composition comprising lithium magnesium sodium silicate, and the crosslinking composition are separately contained.

The mask base composition and the crosslinking composition of the above-kit are generally outlined above but can be modified as described throughout this disclosure except that the lithium magnesium sodium silicate is not included in the mask base composition. In other words, all embodiments of the disclosure relating to mask base compositions and crosslinking compositions apply to kits comprising such compositions.

The masks of the instant disclosure are particularly effective for the cosmetic treatment of skin (including non-therapeutic treatment of skin), especially the skin of the face and neck. For example, the instant disclosure includes methods for: (1) reducing the appearance of fine lines in skin; (2) reducing the appearance of wrinkles in skin; (3) improving the appearance of skin tone and/or skin tone evenness; (4) imparting softness to skin; (5) improving the radiance, luminonsity, and/or glow of skin; (6) hydrating the skin; and/or (7) deliver one or more skin active ingredients to the skin. The methods include forming a mask on the skin (as described above), allowing the mask to remain on the skin for a period of time, and removing the mask from the skin.

More exhaustive but non-limiting lists of components useful in the mask base compositions and the crosslinking compositions of the instant disclosure are provided below.

Thickening Agents

The one or more thickening agents may be xanthan gum, guar gum, biosaccharide gum, cellulose, acacia Seneca gum, sclerotium gum, agarose, pechtin, gellan gum, hyaluronic acid. Additionally, the one or more thickeners may include polymeric thickeners selected from the group consisting of ammonium polyacryloyldimethyl taurate, ammonium acryloyldimethyltaurate/VP copolymer, sodium polyacrylate, acrylates copolymers, polyacrylamide, carbomer, and acrylates/C10-30 alkyl acrylate crosspolymer. In some cases, the thickening agent includes ammonium polyacryloyldimethyl taurate and/or sodium polyacrylate.

Many thickening agents are water-soluble, and increase the viscosity of water or form an aqueous gel when the cosmetic composition of the invention is dispersed/dissolved in water. The aqueous solution may be heated and cooled, or neutralized, for forming the gel, if necessary. The thickener may be dispersed/dissolved in an aqueous solvent that is soluble in water, e.g., ethyl alcohol when it is dispersed/dissolved in water. Non-limiting examples of various types of thickeners include:

a. Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the carbomers, which are homopolymers of acrylic acid crosslinked with allyl ethers of sucrose or pentaerytritol. The carbomers are available as the Carbopol 900 series from B.F. Goodrich (e.g., Carbopol® 954). In addition, other suitable carboxylic acid polymeric agents include Ultrez® 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as Carbopol 1342, Carbopol® 1382, Pemulen TR-1, and Pemulen TR-2, from B.F. Goodrich. In other words, examples of carboxylic acid polymer thickeners useful herein are those selected from carbomers, acrylates/C10-C30 alkyl acrylate crosspolymers, and mixtures thereof.

b. Crosslinked Polyacrylate Polymers

The compositions of the instant disclosure can optionally contain crosslinked polyacrylate polymers useful as thickeners or gelling agents including both cationic and nonionic polymers. Examples of useful crosslinked nonionic polyacrylate polymers and crosslinked cationic polyacrylate polymers are those described in U.S. Pat. Nos. 5,100,660, 4,849,484, 4,835,206, 4,628,078 4,599,379 and EP 228,868, which are all incorporated herein by reference in their entirety.

c. Polyacrylamide Polymers

The compositions of the instant disclosure can optionally contain polyacrylamide polymers, especially nonionic polyacrylamide polymers including substituted branched or unbranched polymers. Among these polyacrylamide polymers is the nonionic polymer given the CTFA designation polyacrylamide and isoparaffin and laureth-7, available under the Tradename Sepigel 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

The compositions may also contain thickening and texturising gels of the type as exemplified by the product range called Lubrajel® from United Guardian. These gels have moisturizing, viscosifying, stabilizing properties.

d. Polysaccharides

A wide variety of polysaccharides can be useful herein. "Polysaccharides" refer to gelling agents that contain a backbone of repeating sugar (i.e., carbohydrate) units. Non-limiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1-3) linked glucose units with a (1-6) linked glucose every three units, a commercially available example of which is Clearogel™. CS11 from Michel Mercier Products Inc.

e. Gums

Other thickening and gelling agents useful herein include materials which are primarily derived from natural sources. Nonlimiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, biosacharide gum, and mixtures thereof.

Additional examples of water-soluble thickeners include water-soluble natural polymers, water-soluble synthetic polymers, clay minerals and silicic anhydride. Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, farcelluran, agar, high-methoxy pectin, low-methoxy pectin, xanthine, chitosan, starch (for example starch derived from corn, potato, wheat, rice, sweet potato and tapioca, a-starch, soluble starch), fermentation polysaccharide (for example, xanthan gum, pullulan, carciran, dextran), acidic heteropolysaccharide derived from callus of plants belonging to Polyantes sp. (for example, tuberous polysaccharide), proteins (for example, sodium casein, gelatin, albumin), chondroitin sulfate, and hyaluronic acid.

Non-limiting examples of water-soluble synthetic polymers include polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, hydroxypropyl starch).

Skin Active Ingredients

The mask base composition or the crosslinking composition may include oen or more skin-active ingredients. Non-limiting examples of active skin-agents include adenosine, 2-[4-(2-hydroxyethyl)piperazin-1-yl]ethanesulfonic acid (HEPES), hyaluronic acid, lanolin, citric acid, malic acid, lactic acid, tartaric acid, salicylic acid, vitamin C, a vitamin, a retinoid, retinal, retinoic acid, a carotenoid, an amino acid, a protein, an enzyme, and a coenzyme. In some cases the skin-active ingredient is adenosine and/or hyaluronic acid. In one embodiment the mask base composition and/or the crosslinking composition comprises a skin-active selected from the group consisting of a humectants or moisturizing ingredient, an anti-aging agent, a depigmenting agent, an anti-wrinkle agent, or an agent that treats oily skin.

Humectants and moisturizing ingredients may be in particular glycerol and its derivatives, urea and its derivatives, especially Hydrovance marketed by National Starch, lactic acid, hyaluronic acid, AHA, BHA, sodium pidolate, xylitol, serine, sodium lactate, ectoin and its derivatives, chitosan and its derivatives, collagen, plankton, an extract of Imperata cylindra sold under the name Moist 24 by Sederma, homopolymers of acrylic acid as Lipidure-HM of NOF Corporation, beta-glucan and in particular sodium carboxymethyl beta-glucan Mibelle-AG-Biochemistry, a mixture of oils passionflower, apricot, corn, and rice bran sold by Nestle under the name NutraLipids, a C-glycoside derivatives, in particular the C-13-D-xylopyranoside-2-hydroxypropane in the form of a solution at 30% by weight of active material in a water/propylene glycol mixture (60/40 wt %) as the product produced by the company Chimex under the trade name "Mexoryl SBB", a rose hip oil marketed by Nestle, a micro-algae extract Prophyridium cruentum enriched with zinc, marketed under the name by Vincience Algualane Zinc spheres of collagen and chondroitin sulfate of marine origin (Atelocollagen) sold by the company Engelhard Lyon under the name Marine Filling Spheres, hyaluronic acid spheres such as those marketed by Engelhard Lyon, and arginine.

Depigmenting agents include vitamin C and its derivatives and especially vitamin CG, CP and 3-O ethyl vitamin C, alpha and beta arbutin, ferulic acid, lucinol and its derivatives, kojic acid, resorcinol and derivatives thereof, tranexamic acid and derivatives thereof, gentisic acid, homogentisic, methyl gentisate or homogentisate, dioic acid, D pantheteine calcium sulphonate, lipoic acid, ellagic acid, vitamin B3, linoleic acid and its derivatives, ceramides and their counterparts, derived from plants such as chamomile, bearberry, the aloe family (vera, ferox, bardensis), mulberry, skullcap, a water kiwi fruit (*Actinidia chinensis*) marketed by Gattefosse, an extract of Paeonia suffruticosa root, such as that sold by Ichimaru Pharcos under the name Liquid Botanpi Be an extract of brown sugar (*Saccharum officinarum*) such as molasses extract marketed by Taiyo Kagaku under the name Liquid Molasses, without this list being exhaustive. Particular depigmenting agents include vitamin C and its derivatives and especially vitamin CG, CP and 3-0 ethyl vitamin C, alpha and beta arbutin, ferulic acid, kojic acid, resorcinol and derivatives, D pantheteine calcium sulfonate, lipoic acid, ellagic acid, vitamin B3, a water kiwi fruit (*Actinidia chinensis*) marketed by Gattefosse, an extract of Paeonia suffruticosa root, such as that sold by the company Ichimaru Pharcos under the name Botanpi Liquid B.

The term "anti-wrinkle active" refers to a natural or synthetic compound producing a biological effect, such as the increased synthesis and/or activity of certain enzymes, when brought into contact with an area of wrinkled skin, this has the effect of reducing the appearance of wrinkles and/or fine lines. Exemplary anti-wrinkle actives may be chosen from: desquamating agents, anti-glycation agents, inhibitors of NO-synthase, agents stimulating the synthesis of dermal or epidermal macromolecules and/or preventing their degradation, agents for stimulating the proliferation of fibroblasts and/or keratinocytes, or for stimulating keratinocyte differentiation reducing agents; muscle relaxants and/or dermo-decontracting agents, anti-free radical agents, and mixtures thereof. Examples of such compounds are: adenosine and its derivatives and retinol and its derivatives such as retinol palmitate, ascorbic acid and its derivatives such as magnesium ascorbyl phosphate and ascorbyl glucoside; tocopherol and derivatives thereof such as tocopheryl acetate, nicotinic acid and its precursors such as nicotinamide; ubiquinone; glutathione and precursors thereof such as L-2-oxothiazolidine-4-carboxylic acid, the compounds C-glycosides and their derivatives as described in particular in EP-1345919, in particular C-beta-D-xylopyranoside-2-hydroxy-propane as described in particular in EP-1345919, plant extracts including sea fennel and extracts of olive leaves, as well as plant and hydrolysates thereof such as rice protein hydrolysates or soybean proteins; algal extracts and in particular laminaria, bacterial extracts, the sapogenins such as diosgenin and extracts of Dioscorea plants, in particular wild yam, comprising: the a-hydroxy acids, f3-hydroxy acids, such as salicylic acid and n-octanoyl-5-salicylic oligopeptides and pseudodipeptides and acyl derivatives thereof, in particular acid {2-[acetyl-(3-trifluoromethyl-phenyl)-amino]-3-methyl-}acetic acid and lipopeptides marketed by the company under the trade names SEDERMA Matrixyl 500 and Matrixyl 3000; lycopene, manganese salts and magnesium salts, especially gluconates, and mixtures thereof.

As adenosine derivatives include especially non-phosphate derivatives of adenosine, such as in particular the 2'-deoxyadenosine, 2',3'-adenosine isopropoylidene; the toyocamycine, 1-methyladenosine, N-6-methyladenosine; adenosine N-oxide, 6-methylmercaptopurine riboside, and the 6-chloropurine riboside.

Other derivatives include adenosine receptor agonists such as adenosine adenosine phenylisopropyl ("PIA"), 1-methylisoguanosine, N6-cyclohexyladenosine (CHA), N6-cyclopentyladenosine (CPA), 2-chloro-N6-cyclopentyladenosine, 2-chloroadenosine, N6-phenyladenosine, 2-phenylaminoadenosine, MECA, N6-phenethyladenosine, 2-p-(2-carboxy-ethyl) phenethyl-amino-5'-N-ethylcarboxamido adenosine (CGS-21680), N-ethylcarboxamido-adenosine (NECA), the 5'(N-cyclopropyl)-carboxamidoadenosine, DPMA (PD 129.944) and metrifudil.

In one embodiment the cosmetic composition comprises an active ingredient that addresses oily skin. These actives can be sebo-regulating or antiseborrhoeic agents capable of regulating the activity of sebaceous glands. These include: retinoic acid, benzoyl peroxide, sulfur, vitamin B6 (pyridoxine or) chloride, selenium, samphire—the cinnamon extract blends, tea and octanoylglycine such as—15 Sepicontrol A5 TEA from Seppic—the mixture of cinnamon, sarcosine and octanoylglycine marketed especially by Seppic under the trade name Sepicontrol A5—zinc salts such as zinc gluconate, zinc pyrrolidonecarboxylate (or zinc pidolate), zinc lactate, zinc aspartate, zinc carboxylate, zinc salicylate 20, zinc cysteate;—derivatives particularly copper and copper pidolate as *Cuivridone Solabia*—extracts from plants of *Arnica montana, Cinchona succirubra, Eugenia caryophyllata, Humulus lupulus, Hypericum perforatum, Mentha pipenta* 25 *Rosmarinus officinalis, Salvia officinalis* and *Thymus vulgaris*, all marketed for example by Maruzen—extracts of meadowsweet (*Spiraea ulmaria*), such as that sold under the name Sebonormine by Silab—extracts of the alga *Laminaria saccharina*, such as that sold under the 30 name Phlorogine by Biotechmarine—the root extracts of burnet mixtures (*Sanguisorba officinalis/Poterium officinale*), rhizomes of ginger (*Zingiber officinalis*) and cinnamon bark (*Cinnamomum cassia*), such as that sold under the name Sebustop by Solabia—extracts of flaxseed such as that sold under the name Linumine by Lucas Meyer—*Phellodendron* extracts such as those sold under the name *Phellodendron* extract BG by Maruzen or Oubaku liquid B by Ichimaru Pharcos—of argan oil mixtures extract of *Serenoa serrulata* (saw palmetto) extract and sesame seeds such as that sold under the name Regu SEB by Pentapharm—mixtures of extracts of willowherb, of *Terminalia chebula, nasturtium* and of bioavailable zinc (microalgae), such as that sold under the name Seborilys Green Tech;—extracts of *Pygeum afrianum* such as that sold under the name *Pygeum afrianum* sterolic lipid extract by Euromed—extracts of *Serenoa serrulata* such as those sold under the name Viapure Sabal by Actives International, and those sold by the company Euromed—of extracts of plantain blends, *Berberis aquifolium* and sodium salicylate 20 such as that sold under the name Seboclear Rahn—extract of clove as that sold under the name Clove extract powder by Maruzen—argan oil such as that sold under the name Lipofructyl Laboratories Serobiologiques; 25—lactic protein filtrates, such as that sold under the name Normaseb by Sederma—the seaweed *laminaria* extracts, such as that sold under the name Laminarghane by Biotechmarine—oligosaccharides seaweed *Laminaria digitata*, such as that sold under the name Phycosaccharide 30 AC by the company Codif—extracts of sugar cane such as that sold under the name Policosanol by the company Sabinsa, the sulfonated shale oil, such as that sold under the name Ichtyol Pale by Ichthyol—extracts of 'meadowsweet (*Spiraea ulmaria*) such as that sold under the name Cytobiol Ulmaire by societeLibiol—sebacic acid, especially sold in the form of a sodium polyacrylate gel under the name Sebosoft by Sederma—glucomannans extracted from konjac tuber and modified with alkylsulfonate chains such as that sold under the name Biopol Beta by Arch Chemical—extracts of *Sophora angustifolia*, such as those sold under the name *Sophora* powder or *Sophora* extract by Bioland—extracts of cinchona bark succirubra such as that sold under the name Red Bark HS by Alban Muller—extracts of *Quillaja saponaria* such as that sold under the name 15 Panama wood HS by Alban Muller—glycine grafted onto an undecylenic chain, such as that sold under the name Lipacide UG OR by SEPPIC—the mixture of oleanolic acid and nordihydroguaiaretic acid, such as that sold under the form of a gel under the name AC.Net by Sederma; 20—phthalimidoperoxyhexanoic acid—citrate tri (C12-C13) sold under the name COSMACOL ECI by Sasol; trialkyl citrate (C14-C15) sold under the name COSMACOL ECL by Sasol—10-hydroxydecanoic acid, including mixtures acid-hydroxydecanoic October 25, sebacic acid and 1,10-decandiol such as that sold under the name Acnacidol BG by Vincience and mixtures thereof.

Implementation of the instant disclosure is provided by way of the following examples. The examples serve to illustrate the technology without being limiting in nature.

EXAMPLE 1

Mask Base Compositions

| Function | Ingredient | A wt. % | B wt. % | C wt. % | D wt. % | E wt. % |
|---|---|---|---|---|---|---|
| Alginate | SODIUM ALGINATE | 2 | 2 | 2 | 2 | 2 |
| Hectorite or Laponite | LITHIUM MAGNESIUM SODIUM SILICATE | | 3 | | | |
| Kaolin Montmorillonite | KAOLONITE HYDRATED ALUMINUM SILICATE | | | 3 | 2 | |
| Mica | ALUMINIUM FLUORO MAGNESIUM SODIUM SILICATE | | | | | 3 |
| Water-Soluble Solvent | GLYCERIN | 9.3 | 9.3 | 9.3 | 9.3 | 9.3 |
| Water | WATER | q.s. 100% | q.s. 100% | q.s. 100% | q.s. 100% | q.s. 100% |

Formulations A-E were used to create films and the elongation (elongation to break) of the films was determined. Each of the mask base compositions of Formulations A-E were separately spread onto glass plates at a thickness of approximately 200 μm. A crosslinking composition of 5% aqueous calcium chloride was sprayed onto the mask base compositions (which were spread on glass plates) at a rate of 5 grams of solution per 100 $cm^2$ of mask base composition. After the resulting films were allowed to crosslink for five minutes at ambient temperature (about 25° C.), the films were removed from the glass plates and subjected to elongation testing to determine the elongation to break.

Elongation testing was carried out in triplicate for each of the films formed. A 5-cm long strip of each film was attached to two plates/holders having a gap (distance from each of the plates from each other) of 1.2 cm. The initial length of each 5-cm long strip located between the plates/holders was 1.6 cm. The two plates/holders were slowly moved apart from each other in order to stretch the films. The time to taut (approximate time before the tensional force is greater than zero) was approximately 8 seconds. The deformation value is the amount film stretched beyond its initial length. For example, in the case of Trial 1 for formulation A, the deformation length is 1.4 and therefore the total length would have been 3.0 cm at the point of breaking (1.4+1.6=3.0). Thus, the % Elongation to break of 88% is calculated as 1.4/1.6 (Amount beyond initial value/Initial value). Data from the testing is presented in the table below.

| Formulation | | Trial 1 | Trial 2 | Trial 3 | Avg. | Std. |
|---|---|---|---|---|---|---|
| A | Deformation (cm) | 1.4 | 1.15 | 1.2 | | |
| | % Elongation to break | 88% | 72% | 75% | 78% | 7% |
| B | Deformation (cm) | 3.9 | 3.6 | 3.35 | | |
| | % Elongation to break | 244% | 225% | 209% | 226% | 14% |
| C | Deformation (cm) | 1.17 | 1.85 | 1.78 | | |
| | % Elongation to break | 73% | 116% | 111% | 100% | 24% |
| D | Deformation (cm) | 2.14 | 1.30 | 1.87 | | |
| | % Elongation to break | 134% | 81% | 117% | 111% | 27% |

-continued

| Formulation | | Trial 1 | Trial 2 | Trial 3 | Avg. | Std. |
|---|---|---|---|---|---|---|
| E | Deformation (cm) | 1.81 | 1.45 | 1.6 | | |
| | % Elongation to break | 113% | 91% | 100% | 101% | 11% |

The data in the above-table shows that films made with lithium magnesium sodium silicate (laponite/hectorite) were surprisingly more elastic than films made with other smectite clays and surprisingly more elastic than films made with mica.

EXAMPLE 2

Addition Examples of Mask Base Compositions

Formulations F-H represent mask base compositions according to the instant disclosure.

| | INCI US | Formulation F wt. % |
|---|---|---|
| Alginate | ALGINATE | 3 |
| Hectorite | LITHIUM MAGNESIUM SODIUM SILICATE | 3 |
| Water-Soluble | GLYCERIN | 10 |
| Solvent | PROPYLENE GLYCOL | 3 |
| Salts | CITRIC ACID/SODIUM CITRATE | 0.1 |
| Preservative | SODIUM BENZOATE, POTASSIUM SORBATE, CAPRYLYL GLYCOL | 0.7 |
| Thickener | LOCUST BEAN GUM | 0.1 |
| Skin Active | VITAMIN C | 0.1 |
| Optional Fragrances | PERFUMES | ≤2 |
| Water | WATER | q.s. 100% |

| | INCI US | Formulation G wt. % |
|---|---|---|
| Alginate | ALGINATE | 3 |
| Hectorite | LITHIUM MAGNESIUM SODIUM SILICATE | 3 |
| Water-Soluble | GLYCERIN | 10 |
| Solvent | PENTYLENE GLYCOL | 3 |
| Salts | SODIUM CARBONATE AND/OR SODIUM BICARBONATE | 0.1 |
| Preservative | SODIUM BENZOATE, POTASSIUM SORBATE, CAPRYLYL GLYCOL | 0.7 |
| Thickener | XANTHAN GUM | 0.1 |
| Skin Active | CAFFEINE AND/OR NIACINAMIDE | 0.1 |
| Optional Fragrances | PERFUMES | ≤2 |
| Water | WATER | q.s. 100% |

| | INCI US | Formulation H wt. % |
|---|---|---|
| Alginate | ALGINATE | 3 |
| Hectorite | LITHIUM MAGNESIUM SODIUM SILICATE | 3 |
| Water-Soluble | GLYCERIN | 10 |
| Solvent | HYDROXYETHYL UREA | 3 |
| Salts | DIPOTASSIUM PHOSPHATE, POTASSIUM PHOSPHATE, DISODIUM EDTA | 0.1 |
| Preservative | SODIUM BENZOATE, POTASSIUM SORBATE, CAPRYLYL GLYCOL | 0.7 |
| Thickener | AMMONIUM ACRYLOYLDIMETHYL TAURATE/VP COPOLYMER | 0.1 |
| Skin Active | ADENOSINE | 0.1 |
| Optional Fragrances | PERFUMES | ≤2 |
| Water | WATER | q.s. 100% |

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the inventive concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" (or "comprise," "have," and "include") are used in their open, non-limiting sense.

The terms "a," "an," and "the" are understood to encompass the plural as well as the singular.

Thus, the term "a mixture thereof" also relates to "mixtures thereof." Throughout the disclosure, if the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counterion. This list of counterions, however, is non-limiting.

The expression "one or more" means "at least one" and thus includes individual components as well as mixtures/combinations.

Other than in the operating examples, or where otherwise indicated, all numbers expressing quantities of ingredients and/or reaction conditions can be modified in all instances by the term "about," meaning within +/−5% of the indicated number.

Some of the various categories of components identified for for the compositions of the instant disclosure overlap. In such cases where overlap may exist and the composition/product includes two overlapping components (or more than two overlapping components), an overlapping component does not represent more than one component. For example, a particular component may be defined as both a "thickening agent" and a "skin-active agent." If a particular composition/product includes both a thickening agent and a skin-active agent, a single component can serve as only a thickening agent or a skin-active agent (a single component does not serve as both the thickening agent and the skin-active agent).

All percentages, parts and ratios herein are based upon the total weight of the compositions of the present invention, unless otherwise indicated.

The term "treat" (and its grammatical variations) as used herein refers to the application of the compositions of the instant disclosure onto a surface such as the skin. The term 'treat,' and its grammatical variations, relates to contacting skin with the compositions of the instant disclosure.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically 1, 2, 3, 4 and 5, as well as sub ranges such as 2-5, 3-5, 2-3, 2-4, 1-4, etc.

All components that are positively set forth in the instant disclosure may be negatively excluded from the claims, e.g., a claimed composition may be "free," "essentially free" (or "substantially free") of one or more components that are positively set forth in the instant disclosure.

All publications and patent applications cited in this specification are herein incorporated by reference, and for any and all purposes, as if each individual publication or patent application were specifically and individually indicated to be incorporated by reference. In the event of an inconsistency between the instant disclosure and any publications or patent application incorporated herein by reference, the instant disclosure controls.

The invention claimed is:

1. A method for improving film elasticity of a mask, the method comprising:
    (a) applying a mask base composition onto a surface, the mask base composition comprising:
        (i) alginic acid and/or a salt thereof;
        (ii) lithium magnesium sodium silicate;
        (iii) one or more water-soluble solvents selected from glycerin, alcohols, organic solvents, polyols, glycols, and a mixture thereof; and
        (iv) water;
            wherein the weight ratio of the (i) alginic acid and/or a salt thereof to the (ii) lithium magnesium sodium silicate is about 1:1 to about 1:5; and
    (b) exposing the mask base composition to a crosslinking composition for a time sufficient to crosslink the alginic acid and/or a salt thereof and form a final mask, the crosslinking composition being an aqueous liquid comprising:
        (i) one or more polyvalent cations of one or more metals; and
        (ii) water.

2. The method of claim 1, wherein the thickness of the final mask is 1-10 mm, and wherein the final mask has an elongation to break at 25° C. that is at least 10% higher than that of an analogous mask not comprising lithium magnesium sodium silicate.

3. The method of claim 1, wherein time sufficient to crosslink the alginate and form a final mask is one minute or less.

4. The method of claim 1, wherein the mask base composition is exposed to the crosslinking composition by spraying the crosslinking composition onto the mask base composition that is applied to the surface.

5. The method of claim 1, wherein the final mask is a cream, paste, gel, or a solid composite having an elastic texture.

6. The method of claim 1, wherein the one or more polyvalent cations in the crosslinking composition comprises calcium ions.

7. The method of claim 1, wherein the mask base composition is free of added calcium ions.

8. The method of claim 1, wherein the surface is skin.

9. The method of claim 8, wherein the skin is facial skin of a human.

10. The method of claim 1, wherein at least one of the one or more water-soluble solvents is glycerin.

11. The method of claim 1, wherein the final mask is:
    essentially free of mica;
    essentially free of polymeric film forming polymers other than the alginic acid, salts of alginic acid, and the lithium magnesium sodium silicate;
    essentially free of surfactants and/or emulsifiers; and/or
    essentially free of silicones.

12. The method of claim 1, wherein the mask base composition comprises:
    (i) about 0.1 to about 10 wt. %, based on the total weight of the mask base composition, of alginic acid and/or a salt thereof;
    (ii) about 0.1 to about 20 wt. %, based on the total weight of the mask base composition, of lithium magnesium sodium silicate;
    (iii) about 0.1 to about 50 wt. %, based on the total weight of the mask base composition, of one or more water-soluble solvents; and
    (iv) about 40 to about 95 wt. %, based on the total weight of the mask base composition, of water; and
    the crosslinking composition comprises:
    (i) about 0.1 to about 35 wt. %, based on the total weight of the crosslinking composition, of salt(s) that provide one or more polyvalent cations of one or more metals; and
    (ii) about 50 to about 99 wt. %, based on the total weight of the crosslinking composition, of water.

13. A mask formed by the method of claim 1.

14. A method of treating skin comprising:
    (a) spraying a mask base composition onto the skin, the mask base composition comprising:
        (i) alginic acid and/or a salt thereof;
        (ii) lithium magnesium sodium silicate;
        (iii) one or more water-soluble solvents selected from glycerin, alcohols, organic solvents, polyols, glycols, and a mixture thereof; and
        (iv) water;

wherein the weight ratio of the (i) alginic acid and/or a salt thereof to the (ii) lithium magnesium sodium silicate is about 1:1 to about 1:5; and (b) spraying a crosslinking composition onto the base composition on the skin for a time sufficient to crosslink the alginic acid and/or a salt thereof and form a final mask on the skin, the crosslinking composition comprising:
   (i) one or more polyvalent cations of one or more metals; and
   (ii) water.

15. The method of claim 14, further comprising removing the final mask from the skin.

16. The method of claim 15, wherein removing the final mask from the skin comprises peeling at least a portion of the final mask from the skin.

17. The method of claim 14, wherein the mask base composition comprises:
   (i) about 0.1 to about 10 wt. %, based on the total weight of the mask base composition, of alginic acid and/or a salt thereof;
   (ii) about 0.1 to about 20 wt. %, based on the total weight of the mask base composition, of lithium magnesium sodium silicate;
   (iii) about 0.1 to about 50 wt. %, based on the total weight of the mask base composition, of one or more water-soluble solvents; and
   (iv) about 40 to about 95 wt. %, based on the total weight of the mask base composition, of water; and the crosslinking composition comprises:
   (i) about 0.1 to about 35 wt. %, based on the total weight of the crosslinking composition, of salt(s) that provide one or more polyvalent cations of one or more metals; and
   (ii) about 50 to about 99 wt. %, based on the total weight of the crosslinking composition, of water.

18. A kit for making a mask, the kit comprising
a) a mask base composition comprising:
   (i) alginic acid and/or a salt thereof;
   (ii) lithium magnesium sodium silicate;
   (iii) one or more water-soluble solvents selected from glycerin, alcohols, organic solvents, polyols, glycols, and a mixture thereof; and
   (iv) water;
   wherein the weight ratio of the (i) alginic acid and/or a salt thereof to the (ii) lithium magnesium sodium silicate is about 1:1 to about 1:5; and
b) a crosslinking composition comprising:
   (i) one or more polyvalent cations of one or more metals; and
   (ii) optionally, water;
   wherein the mask base composition and the crosslinking composition are separately contained.

19. The kit of claim 18, wherein the polyvalent cations comprise calcium ions.

* * * * *